United States Patent [19]

Coy et al.

[11] Patent Number: 4,871,717

[45] Date of Patent: Oct. 3, 1989

[54] PEPTIDES

[75] Inventors: David H. Coy, New Orleans; William A. Murphy, Covington, both of La.

[73] Assignee: Administrators of the Tulane Educational Fund, New Orleans, La.

[21] Appl. No.: 1,245

[22] Filed: Jan. 7, 1987

[51] Int. Cl.$^4$ .................. A61K 37/02; C07K 7/26
[52] U.S. Cl. ........................... 514/11; 514/16; 514/17; 530/311; 530/323; 530/329; 530/330
[58] Field of Search ............... 530/311, 323, 329, 330; 514/11, 16, 17

[56] References Cited

U.S. PATENT DOCUMENTS

| | | | |
|---|---|---|---|
| 4,190,648 | 2/1980 | Veber | 514/11 |
| 4,291,022 | 9/1981 | Sandrin | 514/11 |
| 4,395,403 | 7/1983 | Bauer | 514/12 |
| 4,435,385 | 3/1984 | Bauer | 514/11 |
| 4,485,101 | 11/1984 | Coy | 514/11 |
| 4,486,415 | 12/1984 | Freidinger | 514/11 |
| 4,522,813 | 6/1985 | Nutt | 514/11 |
| 4,585,755 | 4/1986 | Morgan | 514/11 |

OTHER PUBLICATIONS

Veber et al. (1984) Life Sciences 34(14), 1371.

*Primary Examiner*—Delbert R. Phillips
*Assistant Examiner*—Christina Chan
*Attorney, Agent, or Firm*—Paul T. Clark

[57] ABSTRACT

Heptapeptide analogs of somatastatin which inhibit secretion of growth hormone.

14 Claims, No Drawings

PEPTIDES

BACKGROUND OF THE INVENTION

This invention relates to therapeutic peptides.

A number of somatostatin analogs exhibiting GH-release-inhibiting activity have been described in the literature, including analogs containing fewer than the naturally occurring fourteen amino acids. For example, Coy et al. U.S. Pat. No. 4,485,101, hereby incorporated by reference, describes dodecapeptides having an N-terminal acetyl group, a C-terminal NH$_2$, D-Trp at position 6, and p-Cl-Phe at position 4. (Herein, when no designation of configuration is given, the L-isomer is intended.)

SUMMARY OF THE INVENTION

In general, the invention features a heptapeptide of the formula:

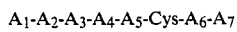

wherein A$_1$ is

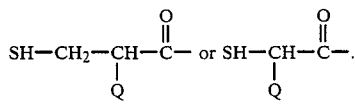

(where Q is H or a C$_1$–C$_8$ alkyl group); A$_2$ is o-, m-, or more preferably, p-substituted X-Phe or X-D-Phe (where X is H, halogen, NH$_2$, NO$_2$, OH, C$_1$–C$_3$ alkyl, or C$_1$–C$_3$ alkoxy); A$_3$ is X-Trp, X-D-Trp, α-N-methyl-X-Trp, or α-N-methyl-D-X-Trp (where X is a substituent on the benzene ring and is H$_1$ halogen, NH$_2$, NO$_2$, OH, C$_1$–C$_3$ alkyl, or C$_1$–C$_3$ alkoxy); A$_4$ is Lys, α-N-methyl-Lys, or ε-N-R$_1$-Lys (where R$_1$ is C$_1$–C$_3$ alkyl); A$_5$ is Val or Thr; A$_6$ is Pro or

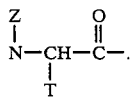

where Z is H or CH$_3$ and T is H, CH$_2$OH, CH$_2$CH$_2$OH, CH$_2$CH$_2$CH$_2$OH, CH(CH$_3$)OH, isobutyl, benzyl (substituted in the o-, m-, or p-positions with H, halogen, NH$_2$, NO$_2$, OH, C$_1$–C$_3$ alkyl, or C$_1$–C$_3$ alkoxy), CH$_2$-β-naphthyl (substituted on the benzene ring with H, halogen, NH$_2$, OH, C$_1$–C$_3$ alkyl, or C$_1$–C$_3$ alkoxy), or CH$_2$-pyridyl (substituted on the benzene ring wtih H, halogen, NH$_2$, NO$_2$, OH, C$_1$–C$_3$ alkyl, or C$_1$–C$_3$ alkoxy); and A$_7$ is OR$_2$ (where R$_2$ is H or C$_1$–C$_3$ alkyl), CH$_2$OH, CH$_2$OCR$_3$ (where R$_3$ is C$_1$–C$_{12}$ alkyl, C$_8$–C$_{12}$ aralkyl, or phenoxy), or

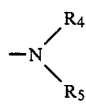

(where R$_4$ is H or C$_1$–C$_3$ alkyl and R$_5$ is H, C$_1$–C$_3$ alkyl, phenyl, or C$_7$–C$_{10}$ aralkyl); or a pharmaceutically acceptable salt thereof.

In the formula given above, the configuration of the molecule at the carbon atom to which T is bonded is not given, indicating that the amino acid residue of which T is a substituent can have the D- or L-configuration.

Preferred compounds of the invention include MPA-Tyr-D-Trp-Lys-Val-Cys-Thr-NH$_2$ (MPA=3-mercaptopropionoyl); MPA-Tyr-D-Trp-Lys-Val-Cys-Phe-NH$_2$; MPA-Tyr-D-Trp-Lys-Val-Cys-p-Cl-Phe-NH$_2$; and MPA-Tyr-D-Trp-Lys-Val-Cys-β-Nal-NH$_2$.

In other preferred embodiments, a therapeutically effective amount of the therapeutic compound and a pharmaceutically acceptable carrier substance, e.g. magnesium carbonate, lactose, or a phospholipid with which the therapeutic compound can form a micelle, together form a therapeutic composition, e.g. a pill, tablet, capsule, or liquid for oral administration to a human patient, a spreadable cream, gel, lotion, or ointment for application to the skin of a human patient in need of the compound, a liquid capable of being administered nasally as drops or spray, or a liquid capable of intravenous, parenteral, subcutaneous, or intraperitoneal administration. The pill, tablet or capsule can be coated with a substance capable of protecting the composition from the gastric acid in the patient's stomach for a period of time sufficient to allow the composition to pass undisintegrated into the patient's small intestine. The therapeutic composition can also be in the form of a biodegradable sustained release formulation for intramuscular administration. For maximum efficacy, zero order release is desired. Zero order release can be obtained using an implantable or external pump, e.g., Infusoid ™ pump, to administer the therapeutic composition.

The compounds of the invention are active in inhibiting the secretion of GH, insulin, and glucagon.

Other features and advantages of the invention will be apparent from the following description of the preferred embodiments thereof, and from the claims.

DESCRIPTION OF THE PREFERRED EMBODIMENTS

Structure

The compounds of the invention have the general formula recited in the Summary of the Invention, above. They are all heptapeptide analogs of somatostatin which have Cys at position 6; this residue forms a ring with the residue at position 1 via a disulfide bond. It has been found that MPA at position 1; Tyr at position 2; D-Trp at position 3; Lys at position 4; and Val at position 5 are modifications which particularly enhance activity.

The compounds can be provided in the form of pharmaceutically acceptable salts. Examples of preferred salts are those with therapeutically acceptable organic acids, e.g., acetic, lactic, maleic, citric, malic, ascorbic, succinic, benzoic, salicylic, methanesulfonic, toluenesulfonic, or pamoic acid, as well as polymeric acids such as tannic acid or carboxymethyl cellulose, and salts with inorganic acids such as the hydrohalic acids, e.g., hydrochloric acid, sulfuric acid, or phosphoric acid.

Synthesis

The synthesis of one heptapeptide follows. Other heptapeptides can be prepared by making appropriate modifications, within the ability of someone of ordinary skill in this field, of the following synthetic method.

The first step in the preparation of MPA-Tyr-D-Trp-Lys-Val-Cys-Thr-NH$_2$ was the preparation of the intermediate S-methylbenzyl-3-MPA-Tyr-D-Trp-N-benzyloxycarbonyl-Lys-Val-S-methylbenzyl-Cys-O-benzyl-Thr-benzhydryl amine resin, as follows.

Benzhydrylamine-polystyrene resin (Vega Biochemicals, Inc.) (1.00 g, 0.5 mmole) in the chloride ion form was placed in the reaction vessel of a Beckman 990B peptide synthesizer programmed to perform the following reaction cycle: (a) methylene chloride; (b) 33% trifluoroacetic acid in methylene chloride (2 times for 1 and 25 min. each); (c) methylene chloride; (d) ethanol; (e) methylene chloride; (f) 10% triethylamine in chloroform.

The neutralized resin was stirred with Boc-O-benzyl-threonine and diisopropylcarbodiimide (1.5 mmole each) in methylene chloride for 1 h; the resulting amino acid resin was then cycled through steps (a) to (g) in the above wash program. Next, the following amino acids (1.5 mmole) were coupled successively by the same procedure: Boc-S-methylbenzyl-cysteine, Boc-Val, Boc-N-benzyloxycarbonyllysine, Boc-D-Trp, Boc-tyrosine, and Boc-S-methylbenzyl-3-mercaptopropionic acid. After washing and drying, the completed resin weighed 1.89 g.

The resin was mixed with anisole (4 ml) and anhydrous hydrogen fluoride (36 ml) at 0° C. and stirred for 45 min. Excess hydrogen fluoride was evaporated rapidly under a stream of dry nitrogen and free peptide precipitated and washed with ether. The crude peptide was then dissolved in 800 ml of 90% acetic acid to which was added $I_2$ in methanol until a permanent brown color was present. The solution was then stirred for 1 h before removing the solvent in vacuo. The resulting oil was dissolved in a minimum volume of 50% acetic acid and eluted on a column (2.5×100 mm) of Sephadex G-25. Fractions containing a major component by uv absorption and thin layer chromatography were then pooled, evaporated to a small volume, and applied to a column (2.5×50 cm) of Whatman LRP-1 octadecylsilane (15–20 uM).

The column was eluted with a linear gradient of 10–50% acetonitrile in 0.1% trifluoroacetic acid in water. Fractions were examined by thin layer chromatography and analytical high performance liquid chromatography and pooled to give maximum purity. Repeated lyophilization of the solution from water yielded 129 mg of the product as a white, fluffy powder.

The product was found to be homogeneous by Hplc and Tlc. Amino acid analysis of an acid hydrolysate and fast atom bombardment mass spectrometry confirmed the composition of the heptapeptide.

The heptapeptides of the invention having the formulae MPA-Tyr-D-Trp-Lys-Val-Cys-Phe-$NH_2$; MPA-Tyr-D-Trp-Lys-Val-Cys-p-Cl-Phe-$NH_2$; and MPA-Tyr-D-Trp-Lys-Val-Cys-$\beta$-Nal-$NH_2$ were made according to methods analogous to those described above.

Use

When administered to mammals, particularly humans, (e.g. orally, topically, intravenously, parenterally in a sustained release, biodegradable form, nasally, or by suppository), the compounds can be effective to inhibit GH release as well as to inhibit insulin, glucagon, and pancreatic exocrine secretion, and to therapeutically affect the central nervous system.

The compounds can be administered to a mammal, e.g. a human, in the dosages used for somatostatin or, because of their greater potency, in smaller dosages. The compounds of the invention can be used for the treatment of cancer, particularly growth hormone-dependent cancer (e.g., bone, cartilage, pancreas (endocrine and exocrine), prostate, or breast), acromegaly and related hypersecretory endocrine states, or of bleeding ulcers in emergency patients and in those suffering from pancreatitis or diarrhea. The compounds can also be used in the management of diabetes and to protect the liver of patients suffering from cirrhosis and hepatitis. The compounds can also be used to treat Alzheimer's disease, as analgesics to treat pain by acting specifically on certain opiate receptors, and as gastric cytoprotective compounds for ulcer therapy. The compounds can also be used to treat certain types of mushroom poisoning.

The compounds can also be used to treat diabetes-related retinopathy. The anti-cancer activity of the compounds may be related to their ability to antagonize cancer-related growth factors such as epidermal growth factor.

The compounds can be administered to a mammal, e.g., a human, in a dosage of 0.01 to 1000 mcg/kg/day, preferably 0.1 to 100 mcg/kg/day.

Other embodiments are within the following claims.

We claim:

1. A heptapeptide of the formula

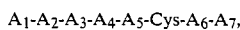

wherein $A_1$ is

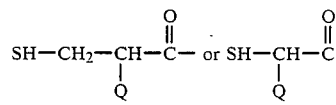

(where Q is H or a $C_1$–$C_8$ alkyl group); $A_2$ is o-, m-, or p-substituted X-Phe or X-D-Phe (where X is H, halogen, $NH_2$, $NO_2$, OH, $C_1$–$C_3$ alkyl, or $C_1$–$C_3$ alkoxy); $A_3$ is X-Trp, X-D-Trp, $\alpha$-N-methyl-X-Trp, or $\alpha$-N-methyl-D-X-Trp (where X is a substituent on the benzene ring and is H, halogen, $NH_2$, $NO_2$, OH, $C_1$–$C_3$ alkyl, or $C_1$–$C_3$ alkoxy); $A_4$ is Lys, $\alpha$-N-methyl-Lys, or $\epsilon$-N-$R_1$-Lys (where $R_1$ is $C_1$–$C_3$ alkyl); $A_5$ is Val or Thr; $A_6$ is Pro or

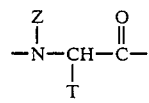

where Z is H or $CH_3$ and T is H, $CH_2OH$, $CH_2CH_2OH$, $CH_2CH_2CH_2OH$, $CH(CH_3)OH$, isobutyl, benzyl (substituted in the o-, m, or p-positions with H, halogen, $NH_2$, $NO_2$, OH, $C_1$–$C_3$ alkyl, or $C_1$–$C_3$ alkoxy), $CH_2$-$\beta$-naphthyl (substituted on the benzene ring with H, halogen, $NH_2$, $NO_2$, OH, $C_1$–$C_3$ alkyl, or $C_1$–$C_3$ alkoxy), or $CH_2$-pyridyl (substituted on the benzene ring with $H_1$ halogen, $NH_2$, OH, $C_1$–$C_3$ alkyl, or $C_1$–$C_3$ alkoxy; and $A_7$ is

(where $R_2$ is H or $C_1$–$C_3$ alkyl), $CH_2OH$, $CH_2OCR_3$ (where $R_3$ is $C_1$–$C_3$ alkyl, $C_8$–$C_{12}$ aralkyl, or phenoxy), or

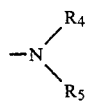

(where $R_4$ is H or $C_1$–$C_3$ alkyl and $R_5$ is H, $C_1$–$C_3$ alkyl, phenyl, or $C_7$–$C_{10}$ aralkyl); or a pharmaceutically acceptable salt thereof.

2. The heptapeptide of claim 1 having the formula 3-mercaptopropionoyl-Tyr-D-Trp-Lys-Val-Cys-Thr-NH$_2$, or a pharmaceutically acceptable salt thereof.

3. The heptapeptide of claim 1 having the formula 3-mercaptopropionoyl-Tyr-D-Trp-Lys-Val-Cys-Phe-NH$_2$, or a pharmaceutically acceptable salt thereof.

4. The heptapeptide of claim 1 having the formula 3-mercaptopropionoyl-Tyr-D-Trp-Lys-Val-Cys-p-Cl-Phe-NH$_2$, or a pharmaceutically acceptable salt thereof.

5. The heptapeptide of claim 1 having the formula 3-mercaptopropionoyl-Tyr-D-Trp-Lys-Val-Cys-$\beta$-Nal-NH$_2$, or a pharmaceutically acceptable salt thereof.

6. A therapeutic composition capable of inhibiting the release of growth hormone, insulin, glucagon, or pancreatic exocrine secretion comprising a therapeutically effective amount of the compound of claim 1 together with a pharmaceutically acceptable carrier substance.

7. A method of treating a mammal in need of reduction of growth hormone, insulin, glucagon, or pancreatic exocrine secretion comprising administering to said mammal a therapeutically effective amount of the compound of claim 1.

8. The therapeutic composition of claim 6 wherein said composition is in the form of a pill, tablet, or capsule for oral administration to a human patient in need of said compound.

9. The therapeutic composition of claim 6 wherein said composition is in the form of a liquid for oral administration to a human patient in need of said compound.

10. The therapeutic composition of claim 8, said composition being coated with a substance capable of protecting said composition from the gastric acid in the stomach of said human patient for a period of time sufficient to allow said composition to pass undisintegrated into the small intestine of said human patient.

11. The therapeutic composition of claim 6, said composition being in the form of a cream, gel, spray, or ointment for application to the skin of a human patient in need of said compound.

12. The therapeutic composition of claim 6, said composition being in the form of a liquid capable of being administered nasally as drops or spray to a human patient in need of said compound.

13. The therapeutic composition of claim 6, said composition being in the form of a liquid for intravenous, subcutaneous, parenteral, or intraperitoneal administration to a human patient in need of said compound.

14. The therapeutic composition of claim 6, said composition being in the form of a biodegradable sustained release composition for intramuscular administration to a human patient in need of said compound.

* * * * *

UNITED STATES PATENT AND TRADEMARK OFFICE
CERTIFICATE OF CORRECTION

PATENT NO. : 4,871,717

DATED : October 3, 1989

INVENTOR(S) : David H. Coy, et al

It is certified that error appears in the above-identified patent and that said Letters Patent is hereby corrected as shown below:

Col. 4, lines 60-65, change the formula by replacing what is shown with "$OR_2$".

Signed and Sealed this

Twenty-eighth Day of August, 1990

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,871,717

DATED : October 3, 1989

INVENTOR(S) : David H. Coy et al.

It is certified that error appears in the above-identified patent and that said Letters Patent is hereby corrected as shown below:

Column 1

As a first sentence and paragraph, insert the paragraph:

--This invention was made in the course of work under a grant or award from the U.S. government; therefore, the U.S. government has rights in the invention.--

Signed and Sealed this

Twenty-fourth Day of December, 1991

Attest:

HARRY F. MANBECK, JR.

Attesting Officer

Commissioner of Patents and Trademarks